(12) United States Patent
Katsikis et al.

(10) Patent No.: US 8,263,080 B2
(45) Date of Patent: Sep. 11, 2012

(54) USE OF AGONISTS AND ANTAGONISTS OF IL-23 IN THE TREATMENT OF VIRAL INFECTION

(75) Inventors: Peter D. Katsikis, Merion Station, PA (US); Ioannis Dimitriou, Philadelphia, PA (US); Daniel J. Cua, Boulder Creek, CA (US)

(73) Assignee: Schering Corporation, Rahway, NJ (US)

( * ) Notice: Subject to any disclaimer, the term of this patent is extended or adjusted under 35 U.S.C. 154(b) by 357 days.

(21) Appl. No.: 11/059,114

(22) Filed: Feb. 15, 2005

(65) Prior Publication Data

US 2005/0208052 A1  Sep. 22, 2005

Related U.S. Application Data

(60) Provisional application No. 60/545,708, filed on Feb. 17, 2004.

(51) Int. Cl.
*A61K 39/395* (2006.01)
*A61K 39/12* (2006.01)
*A61K 39/145* (2006.01)

(52) U.S. Cl. ................. 424/145.1; 424/204.1; 424/209.1
(58) Field of Classification Search .................. None
See application file for complete search history.

(56) References Cited

U.S. PATENT DOCUMENTS

| | | | | |
|---|---|---|---|---|
| 6,811,780 B2* | 11/2004 | Furfine et al. | ........... | 424/145.1 |
| 2003/0017617 A1* | 1/2003 | Chirica et al. | ........... | 436/518 |
| 2003/0124123 A1* | 7/2003 | Giles-Komar et al. | ..... | 424/145.1 |
| 2004/0156849 A1* | 8/2004 | Gurney | ............... | 424/145.1 |
| 2004/0213761 A1* | 10/2004 | Bowman et al. | ........... | 424/85.2 |
| 2004/0219096 A1* | 11/2004 | De Waal Malefyt et al. | ........... | 424/1.41 |
| 2004/0219150 A1* | 11/2004 | Cua et al. | ............... | 424/145.1 |
| 2004/0223969 A1* | 11/2004 | Oft et al. | ................ | 424/145.1 |
| 2004/0258686 A1* | 12/2004 | Chirica et al. | ........... | 424/143.1 |
| 2005/0137385 A1* | 6/2005 | Benson et al. | ........... | 530/388.23 |
| 2005/0147607 A1* | 7/2005 | Reed | ............... | 424/145.1 |

OTHER PUBLICATIONS

Belz et al., Compromised Influenza Virus-Specific CD8+-T-Cell Memory in CD4+-T-Cell-Deficient Mice, 2002, Journal of Virology, vol. 76, No. 23, pp. 12388-12393.*
Holscher, The power of combinatorial immunology: IL-12 and IL-12-related dimeric cytokines in infectious diseases, 2004 (Epub Jun. 27, 2003), Medical Microbiology and Immunology, vol. 193, pp. 1-17.*
Pirhonen, et al. (2002) *J. of Immunol.* 169(10):5673-5678 "Regulation of virus-induced IL-12 and IL-23 expression in human macrophages".
Broberg, et al. (2002) *J. of Interferon and Cytokine Research* 22(6):641-651 "Herpes simplex virus type 1 infection induces upregulation of interleukin-23 (p19) mRNA expression in trigeminal ganglia of BALB/c mice".
Oppmann, et aL (2000) *Immunity* 13(5):715-725 "Novel p19 protein engages IL-12p40 to form a cytokine, IL-23, with biological activities similar as well as distinct from IL-12".
Arulanandam, et al. (1999) *J. Infect. Dis.* 180:940-949 "Intranasal Interleukin-12 is a Powerful Adjuvant for Protective Mucosal Immunity".
Belz, et al. (1998) *Proc. Natl. Acad. Sci. USA* 95:13812-13817 "Characteristics of virus-specific CD8+ T cells in the liver during the control and resolution phases of influenza pneumonia".
Belz, et al. (2000) *J. Virol.* 74:3486-3493 "A Previously Unrecognized H-2D$^b$-Restricted Peptide Prominent in the Primary Influenza A Virus-Specific CD8$^+$ T-Cell Response Is Much Less Apparent following Secondary Challenge".
Bender, et al. (1995) *J. Exp. Med.* 182:1663-1671 "Inactivated Influenza Virus, when presented on dendritic cells, elicits human CD8$^+$ cytolytic T Cell Responses".
Broberg, et al. (2002) *J. Interferon Cytokine Res.* 22:641-651 "Herpes Simplex Virus Type 1 Infection Induces Upregulation of Interleukin-23 (p19) mRNA Expression in Trigeminal Ganglia of BALB/c Mice".
Brombacher, et al. (2003) *Trends Immunol.* 24:207-212 "Novel IL-12 family members shed light on the orchestration of Th1 responses".
Butz and Bevan (1998) *Immunity* 8:167-175 "Massive expansion of Antigen-specific CD8$^+$ T Cells during an acute virus infection".
Clerici, et al. (1993) *Science* 262:1721-1724 Restoration of HIV-specific cell-mediated immune responses by interleukin-12 in vitro.
Cooper, et al. (2002) *J. Immunol.* 168:1322-1327 "Mice lacking bioactive IL-12 can generate protective, antigen-specific cellular responses to mycobacterial infection only if the IL-12 p40 subunit is present".
Cousens, et al. (1999) *J. Exp. Med.* 189:1315-1328 "Two roads diverged: Interferon α/β- and Interleukin 12-mediated pathways in promoting T cell Interferon γ responses during viral infection".
Crowe et al. (2003) *J. Exp. Med.* 198:399-410 "Differential antigen presentation regulates the changing patters of CD8$^+$ T cell immunodominance in primary and secondary influenza virus infections".
De Jong, et al. (1997) *J. Immunol.* 159:786-793 "IL-2 and IL-12 act in synergy to overcome antigen-specific T cell unresponsiveness in mycobacterial disease".
Doherty, et al. (1997) *Immunol. Rev.* 159:105-117 "Effector CD4$^+$ and CD8$^+$ T-cell mechanisms in the control of respiratory virus infections".
Elkins, et al. (2002) *Infection Immunity* 70:1936-1948 "In vivo clearance of an intracellular bacterium, *Francisella tularensis* LVS, is dependent on the p40 subunit of interleukin-12 (IL-12) but not on IL-12 p70".
Elsawa and Bost (2004) *J. Immunol.* 172:516-524 "Murine γ-herpesvirus-68-induced IL-12 contributes to the control of latent viral burden, but also contributes to viral-mediated leukocytosis".
Ely, et al. (2003) *J. Immunol.* 170:1423-1429 "Nonspecific recruitment of memory CD8+ T cells to the lung airways during respiratory virus infections".
Epstein, et al. (1998) *J. Immunol.* 160:322-327 "Mechanism of protective immunity against influenza virus infection in mice without antibodies".

(Continued)

*Primary Examiner* — Benjamin P Blumel

(74) *Attorney, Agent, or Firm* — Gregory R. Bellomy

(57) ABSTRACT

Provided are methods of modulating cytokine activity, e.g., for the purpose of treating viral infections. Also provided are reagents for use in screening for agonists or antagonists of IL-23.

13 Claims, No Drawings

OTHER PUBLICATIONS

Fernandez, et al . (1999) *J. Immunol.* 162:609-617 "High frequency of specific CD8+ T cells in the tumor and blood is associated with efficient local IL-12 gene therapy of cancer".

Fischer, et al. (1997) *Nature Biotechnol.* 15:142-145 "A bioactive designer cytokine for human hematopoietic progenitor cell expansion".

Foss, et al. (2002) *Viral Immunol.* 15:557-566 "Adjuvant danger signals increase the immune response to porcine reproductive and respiratory syndrome virus".

Graham and Braciale (1997) *J. Exp. Med.* 186:2063-2068 "Resistance to and recovery from lethal influenza virus infection in B lymphocyte-deficient mice".

Graham, et al. (1993) *J. Exp. Med.* 178:1725-1732 "Response to influenza infection in mice with a targeted disruption in the interferon γ gene".

Ha, et al. (2004) *J. Immunol.* 172:525-531 "IL-23 induces stronger sustained CTL and Th1 immune responses than IL-12 in hepatitis C virus envelope protein 2 DNA immunization".

Harty, et al. (2000) Annu. Rev. Immunol. 18:275-308 "CD8+ T cell effector mechanisms in resistance in infection".

Hogan, et al. (2001) *J. Immunol.* 166:1813-1822 "Activated antigen-specific CD8+ T cells persist in the lungs following recovery from respiratory virus infections".

Jameson, et al. (1999) *J. Immunol.* 162:7578-7583 "Human CD8+ and CD4+ T lymphocyte memory to influenza a viruses of swine and avian species".

Julkunen, et al. (2001) *Cytokine Growth Factor Revs.* 12:171-180 "Molecular pathogenesis of influenza A virus infection and virus-induced regulation of cytokine gene expression".

Julkunen, et al. (2001) *Vaccine* 19:S32-S37 "Inflammatory responses in influenza A virus infection".

Kaech and Ahmed (2003) *Science* 300:263-265 "CD8 T Cells remember with a little help".

Knutson and Disis (2004) *Clin. Exp. Immunol.* 135:322-329 IL-12 enhances the generation of tumour antigen-specific Th1 CD4 T cells during ex vivo expansion.

Krug, et al. (2003) *Virology* 309:181-189"Intracellular warfare between human influenza viruses and human cells: the roles of the viral NS1 protein".

Leonard, et al. (1997) *Blood* 90:2541-2548 "Effects of single-dose interleukin-12 exposure on interleukin-12-associated toxicity and interferon-γ production".

Lo, et al. (2003) *J. Immunol.* 171:600-607 "Antitumor and Antimetastatic activity of IL23".

Lohr, et al. (2002) *Clin. Exp. Immunol.* 130:107-114 "Reduced virus specific T helper cell induction by autologous dendritic cells in patients with chronic hepatitis B—restoration by exogenous interleukin-12".

Mbawuike, et al. (1999) *J. Infect. Dis.* 180:1477-1486 "Human interleukin-12 enhances interferon-gamma-producing influenza-specific memory CD8+ cytotoxic T lymphocytes".

Miller, et al. (1995) *J. Immunol.* 155:4817-4828 "Nonviable bacterial antigens administered with IL-12 generate antigen-specific T cell responses and protective immunity against *Listeria monocytogenes*".

Monteiro, et al. (1998) *J. Virol.* 72:4825-4831 "Role of interleukin-12 in primary influenza virus infection".

Murali-Krishna, et al. (1998) *Immunity* 8:177-187 "Counting antigen-specific CD8 T cells: a reevaluation of bystander activation during viral infection".

Nagai, et al. (2003) *J. Immunol.* 171:5233-5243 "Timing of IFN-β exposure during human dendritic cell maturation and naïve Th cell stimulation has contrasting effects on Th1 subset generation: a role for IFN-β-mediated regulation of IL-12 family cytokines and IL-18 in native Th cell differentiation".

Naylor and Hadden (2003) *Int. Immunopharmacol.* 3:1205-1215 "T cell targeted immune enhancement yields effective T cell adjuvants".

Nguyen, et al. (2000) *J. Virol.* 74:5495-5501 "Gamma interferon is not required for mucosal cytotoxic T-lymphocyte responses or heterosubtypic immunity to influenza A virus infection in mice".

Oppmann, et al. (2000) *Immunity* 13:715-725 "Novel p19 protein engages IL-12p40 to form a cytokine, IL-23, with biological activities similar as well as distinct from IL-12".

Orange, et al. (1995) *J. Exp. Med.* 181:901-914 "Mechanism of interleukin 12-mediated toxicities during experimental viral infections: role of tumor necrosis factor and glucocorticoids".

Parham, et al. (2002) *J. Immunol.* 168:5699-5708 "A receptor for the heterodimeric cytokine IL-23 is composed of IL-12Rβ1 and a novel cytokine receptor subunit, IL-23R".

Peters, et al.(1998) *J. Immunol.* 161:3575-3581 "In vivo and in vitro activities of the gp130-stimulating designer cytokine hyper-IL-6".

Pirhonen, et al. (2002) *J. Immunol.* 169:5673-5678 "Regulation of virus-induced IL-12 and IL-23 expression in human macrophages".

Rakemann, et al. (1999) *J. Biol. Chem.* 274:1257-1266 "The designer cytokine hyper-interleukin-6 is a potent activator of STAT3-dependent gene transcription in Vivo and in Vitro".

Roman, et al. (2002) *J. Exp. Med.* 196:957-968 "CD4 effector T cell subsets in the response to influenza: heterogeneity, migration, and function".

Sangster, et al. (2003) *J. Exp. Med.* 198:1011-1021 "An early CD4+ T cell-dependent immunoglobulin a response to influenza infection in the absence of key cognate T-B interactions".

Seaman, et al. (2004) *J. Virol.* 78:206-215 "Subsets of memory cytotoxic T lymphocytes elicited by vaccination influence the efficiency of secondary expansion in vivo".

Stiver (2003) *Canadian Medical Assoc. J.* 168:49-57 "The treatment of influenza with antiviral drugs".

Sun and Bevan (2003) *Science* 300:339-342 "Defective CD8 T cell memory following acute infection without CD4 T cell help".

Topham, et al. (2001) *J. Immunol.* 167:6983-6990 "The role of antigen in the localization of naïve, acutely activated, and memory CD8+ T cells to the lung during influenza pneumonia".

Trinchieri (2003) *Nature Revs. Immunol.* 3:133-146 "Interluekin-12 and the regulation of innate resistance and adaptive immunity".

Tsurita, et al. (2001) *J. Pharmacol. Exp. Therapeutics* 298:362-368 "Early augmentation of interleukin (IL)-12 level in the airway of mice administered orally with clarithromycin of intranasally with IL-12 results in alleviation of influenza infection".

Turner, et al. (2001) *J. Immunol.* 167:2753-2758 "Concurrent naive and memory CD8+ T cell responses to an influenza A virus".

Turner, et al. (2003) *Immunity* 18:549-559 "Analysis of clonotype distribution and persistence for an influenza virus-specific CD8+ T cell response".

Van Benten, et al. (2001) *Allergy* 56:949-956 "Prolonged nasal eosinophilia in allergic patients after common cold".

Van Der Meide, et al. (2002) *Vaccine* 20:2296-2302 "Stimulation of both humoral and cellular immune responses to HIV-1 gp120 by interleukin-12 in Rhesus macaques".

Walzl, et al. (2000) *J. Exp. Med.* 192:1317-1326 "Influenza virus lung infection protects from respiratory syncytial virus-induced immunopathology".

Webby, et al. (2003) *Proc. Natl. Acad. Sci. USA* 100:7235-7240 "Protection and compensation in the influenza virus-specific CD8+ T cell response".

Wiley, et al. (2001) *J. Immunol.* 167:3293-3299 "Antigen-specific CD8+ T cells persist in the upper respiratory tract following influenza virus infection".

Wohlleben, et al. (2003) *J. Immunol.* 170:4601-4611 "Influenza A virus infection inhibits the efficient recruitment of Th2 cells into the airways and the development of airway eosinophilia".

Wong and Pamer (2003) *Annu. Rev. Immunol.* 21:29-70 "CD8 T cell responses to infectious pathogens".

Woodland, et al. (2001) *Immunol. Res.* 24:53-67 "Cellular immunity and memory to respiratory virus infections".

Yamamoto, et al. (2001) *J. Virology* 75:499-505 "Immune response induced by airway sensitization after influenza A virus infection depends on timing of antigen exposure in mice".

Yewdell and Garcia-Sastre (2002) *Curr. Opin. Microbiol.* 5:414-418 "Influenza virus still surprises".

Happel, et al. (2003) *J. of Immunol.* 170:4432-4436 "Cutting Edge: Roles of Toll-Like Receptor 4 and IL-23 in IL-17 Expression in Response to *Klebsiella pneumoniae* Infection".

* cited by examiner

USE OF AGONISTS AND ANTAGONISTS OF IL-23 IN THE TREATMENT OF VIRAL INFECTION

This filing is a U.S. Patent Application which claims benefit of U.S. Provisional Patent Application No. 60/545,708, filed Feb. 17, 2004, which is incorporated herein by reference.

FIELD OF THE INVENTION

The present invention relates generally to uses of mammalian cytokines. More specifically, the invention discloses cytokine function in treating influenza virus.

BACKGROUND OF THE INVENTION

The immune system protects individuals from infective agents, e.g., viruses, bacteria, multi-cellular organisms, and cancers. This system includes several types of lymphoid and myeloid cells such as monocytes, macrophages, dendritic cells (DCs), eosinophils, T cells, B cells, and neutrophils. These lymphoid and myeloid cells often produce signaling proteins known as cytokines. Immune response includes inflammation, i.e., the accumulation of immune cells systemically or in a particular location of the body. In response to an infective agent or foreign substance, immune cells secrete cytokines which, in turn, modulate immune cell proliferation, development, differentiation, or migration. Cytokines have been implicated in immune response to a number of viral infections (see, e.g., Abbas, et al. (eds.) (2000) *Cellular and Molecular Immunology*, W.B. Saunders Co., Philadelphia, Pa.; Oppenheim and Feldmann (eds.) (2001) *Cytokine Reference*, Academic Press, San Diego, Calif.; Kaufmann, et al. (2001) *Immunobiol.* 204: 603-613; Saurez and Schultz-Cheery (2000) *Dev. Comp. Immunol.* 24: 269-283; van Reeth and Nauwynck (2000) *Vet. Res.* 31: 187-213; Garcia-Sastre (2001) *Virology* 279: 375-384; Katze, et al. (2002) *Nat. Rev. Immunol.* 2: 675-687; van Reeth (2000) *Vet. Microbiol.* 74: 109-116; Tripp (2003) *Curr. Pharm. Des.* 9: 51-59).

Influenza virus is a leading viral cause of mortality, contributing to 20,000 deaths in the United States per year. The virus destroys the airway epithelium and can spread to extrapulmonary tissues. High risk individuals include those over the age of 65 years, and those with disorders such as chronic obstructive pulmonary disease (COPD), asthma, chronic heart disease, diabetes, chronic renal or hepatic disease, cancer, or chronic connective tissue disease. Influenza viruses are classified in three types, A, B, and C, of which A is clinically the most important. The genome of the influenza A virus encodes ten proteins. Due to the antigenic variability on the surface proteins, e.g., hemagglutinin and neuramimidase, it has not been possible to produce a vaccine that provides long lasting protection for, e.g., the influenza A virus (IV) strain (see, e.g., Treanor (2004) *New Engl. J. Med.* 350: 218-220; Steinhauer and Skehel (2002) *Annu. Rev. Genet.* 36: 305-332; Mozdzanowska, et al. (2000) *J. Immunol.* 164: 2635-2643; Nicholson, et al. (2003) *The Lancet* 362: 1733-1745).

With influenza infection, virus specific $CD8^+$ T cells occur at elevated concentrations in the respiratory tract, and rapidly express effector functions upon re-exposure to viral antigen. Although influenza virus replication is essentially limited to the respiratory tract, the infection results in activation of immune cells in the respiratory tract, but also elsewhere in the body, e.g., liver. $CD8^+$ T cells combat virus infection through direct lysis of infected cells or by secretion of antiviral cytokines, such as interferon-gamma (IFNgamma) and tumor necrosis factor-alpha (TNFalpha). IFNgamma induces proteins that inhibit viral replication, e.g., through impairing metabolism of viral mRNA and double stranded RNA. Moreover, IFNgamma activates antigen presenting cells (APCs), e.g., by upregulating major histocompatiblity complex (MHC) on the APCs.

Immune response to primary and secondary infection with influenza has different properties, as IFNgamma appears not needed for response to primary infection, but is used for recovery from secondary infection. Another difference is that $CD8^+$ T cell response to acute infections, e.g., early stages of acute viral infection, is relatively independent of $CD4^+$ T cells, whereas response by memory $CD8^+$ T cells in secondary infections, is enhanced by $CD4^+$ T cells. After primary infection with influenza, large pools of memory $CD8^+$ T cells persist in secondary lymph organs, as well as in non-lymphoid tissues, such as lungs and liver (see, e.g., Kaech and Ahmed (2003) *Science* 300: 263-265; Sun and Bevan (2003) *Science* 300: 339-342; Turner, et al. (2003) *Immunity* 18: 549-559; Ely, et al. (2003) *J. Immunol.* 170: 1423-1429; Topham, et al. (2001) *J. Immunol.* 167: 6983-6990).

Further differences between response to primary and secondary viral infections are as follows. Viral peptides bound to MHC Class I molecules stimulate CD8 T cells, where the characteristics of CD8' T cell response, e.g., cytokine production, can differ, depending on the identity of the peptide that is presented and whether the viral infection is primary or secondary. For example, primary infection can involve immune response by T cells specific for influenza nucleoprotein and for influenza acidic polymerase, but during secondary infection, most of the T cells recognize nucleoprotein but not acidic polymerase. After primary exposure, about 12% of CD8' T cells taken from lungs is specific for the $NP_{366-374}$ epitope, while after secondary exposure this figure increases, e.g., to 60-70%. Changes in immune response during primary or secondary infection can reflect changes in the identity of the APC that presents antigen, e.g., a dendritic cell (DC) versus a macrophage, and on differences in the DC's ability versus macrophage's ability to activate a memory T cell during secondary infection (see, e.g., Yewdell and Garcia-Sastre (2002) *Curr. Opin. Microbiol.* 5:414-418; Stiver (2003) *Canadian Medical Assoc. J.* 168:49-57; Nguyen, et al. (2000) *J. Virol.* 74:5495-5501; Graham, et al. (1993) *J. Exp. Med.* 178:1725-1732; Wong and Pamer (2003) *Annu. Rev. Immunol.* 21:29-70; Crowe, et al. (2003) *J. Exp. Med.* 198:399-410; Julkunen, et al. (2001) *Vaccine* 19:S32-S37; Webby, et al. (2003) *Proc. Natl. Acad. Sci. USA* 100:7235-7240; Turner, et al., supra; Wiley, et al. (2001) *J. Immunol.* 167:3293-3299; Belz, et al. (2000) *J. Virol.* 74:3486-3493; Belz, et al. (1998) *Proc. Natl. Acad. Sci. USA* 95:13812-13817).

Long lasting and broad immunity against influenza may depend on the ability to generate $CD8^+$ T cell responses, but generation of this response is often not effective with the current vaccines. There is an unmet need to provide protection against viruses during primary and secondary immune responses, e.g., to influenza virus. The present invention fulfils this need by providing methods of using agonists and antagonists of IL-23 and IL-23 receptor.

SUMMARY OF THE INVENTION

The present invention is based, in part, upon the discovery that an agonist or antagonist of IL-23 modulates immune response to influenza virus.

The present invention provides a method of modulating $CD8^+$ T cell response to a virus, viral antigen, or viral infection, comprising administering an effective amount of an agonist of p19, IL-23, or IL-23R or antagonist of p19, IL-23, or IL-23R. Also provided is the above method wherein the antagonist comprises: a) a binding composition from an antibody that specifically binds to p19, IL-23, or IL-23R; b) a soluble receptor derived from IL-23R that specifically binds to IL-23; c) a small molecule; or d) a nucleic acid that specifically hybridizes to a nucleic acid encoding p19 or IL-23R. Moreover, the present invention provides the above method wherein the binding composition derived from an antibody comprises: a polyclonal antibody; a monoclonal antibody; a humanized antibody, or a fragment thereof, an Fab, Fv, or F(ab')$_2$ fragment; a peptide mimetic of an antibody; or a detectable label, as well as the above method wherein the nucleic acid comprises anti-sense nucleic acid or small interference RNA (siRNA).

In another aspect, the present invention provides a method of modulating CD8$^+$ T cell response to a virus, viral antigen, or viral infection, comprising administering an effective amount of an agonist p19, IL-23, or IL-23R or antagonist of p19, IL-23, or IL-23R, further comprising co-administering an effective amount of an: a) agonist of p35, IL-12, p40, IL-12Rβ1, or IL-12Rβ2; or b) antagonist of p35, IL-12, p40, IL-12Rβ1, or IL-12Rβ2, as well as the above method wherein the agonist of p19, IL-23, or IL-23R decreases: a) the percent of CD8$^+$ T cells that are viral antigen-specific CD8$^+$ T cells; b) the percent of CD8$^+$ T cells that are IFNγ-producing viral antigen-specific CD8$^+$ T cells; or c) cytotoxicity of viral antigen-specific CD8$^+$ T cells. The invention also contemplates the above method wherein the increase comprises an immune response to secondary viral infection, further comprising administering an effective amount of an antagonist of p35, IL-12, p40, IL-12Rbeta1, or IL-12Rbeta2; as well as the above method wherein the antagonist of p19, IL-23, or IL-23R increases the total number of CD8$^+$ T cells during immune response to a secondary viral infection.

In another embodiment, the present invention provides the above method, wherein the total number of CD8$^+$ T cells is of a lung; a bronchoalveolar lavage (BAL); a spleen; or a lymph node, as well as the above method further comprising administrating an effective amount of an antagonist of p35, IL-12, IL-12Rbeta2, or p40.

Yet another aspect of the present invention is a method of modulating CD8$^+$ T cell response to a virus, viral antigen, or viral infection, comprising administering an effective amount of an agonist p19, IL-23, or IL-23R or antagonist of p19, IL-23, or IL-23R; wherein the virus is a respiratory virus; a mucosal virus; or influenza virus; or wherein the influenza virus is influenza A, influenza B, or influenza C; or the above method wherein the viral antigen comprises an influenza virus antigen; as well as the above method wherein the influenza virus antigen is from influenza A virus nucleoprotein or influenza A virus acidic polymerase; or wherein the viral infection comprises a respiratory syndrome or pneumonia. In yet another embodiment, the present invention provides the above method further comprising administering a vaccine or an adjuvant, as well as a method to diagnose a viral infection comprising contacting a binding composition to a biological sample, wherein the binding composition specifically binds to p19, IL-23, or IL-23R; or a nucleic acid encoding p 19 or IL-23R; and measuring or determining the specific binding of the binding composition to the biological sample. The binding composition can be, e.g., an antibody, nucleic acid probe, PCR primer, or molecular beacon.

Provided is a method of treating an influenza A virus infection comprising treating with an effective amount of an agonist or antagonist of p19, IL-23, or IL-23R.

A further embodiment of the present invention provides a kit for the diagnosis of a viral infection comprising a compartment and a binding composition that specifically binds to: a) p19, IL-23, or IL-23R; or b) a nucleic acid encoding p19 or IL-23R.

DETAILED DESCRIPTION OF THE PREFERRED EMBODIMENTS

As used herein, including the appended claims, the singular forms of words such as "a," "an," and "the," include their corresponding plural references unless the context clearly dictates otherwise.

All references cited herein are incorporated herein by reference to the same extent as if each individual publication or patent application was specifically and individually indicated to be incorporated by reference.

I. Definitions

"Activation," "stimulation," and "treatment," as it applies to cells or to receptors, may have the same meaning, e.g., activation, stimulation, or treatment of a cell or receptor with a ligand, unless indicated otherwise by the context or explicitly. "Ligand" encompasses natural and synthetic ligands, e.g., cytokines, cytokine variants, analogues, muteins, and binding compositions derived from antibodies. "Ligand" also encompasses small molecules, e.g., peptide mimetics of cytokines and peptide mimetics of antibodies. "Activation" can refer to cell activation as regulated by internal mechanisms as well as by external or environmental factors. "Response," e.g., of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming.

"Activity" of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" can also mean specific activity, e.g., [catalytic activity]/[mg protein], or [immunological activity]/[mg protein], concentration in a biological compartment, or the like. "Proliferative activity" encompasses an activity that promotes, that is necessary for, or that is specifically associated with, e.g., normal cell division, as well as cancer, tumors, dysplasia, cell transformation, metastasis, and angiogenesis.

An "adjuvant" is a molecule, compound, or composition, that enhances immune response to a vaccine. The present invention provides methods of administering an agonist or antagonist of IL-23 or of p19, in conjunction with an adjuvant, e.g., an interferon or Freund's adjuvant. Adjuvants are described (see, e.g., Proietti, et al. (2002) *J. Immunol.* 169: 375-383; Billiau and Matthys (2001) *J. Leukoc. Biol.* 70: 849-860; Klinman (2003) *Expert Rev. Vaccines* (2003) 2: 305-315; Hamilton (2003) *J Leukocyte Biol.* 73: 702-712; Holmgren, et al. (2003) *Vaccine* 21 (Suppl. 2):S89-S95; Lemieux (2002) *Expert Rev. Vaccines* 1: 85-93; Villinger (2003) *Expert Rev. Vaccines* 2: 317-326).

"Administration" and "treatment," as it applies to an animal, human, experimental subject, cell, tissue, organ, or biological fluid, refers to contact of an exogenous pharmaceutical, therapeutic, diagnostic agent, compound, or composition to the animal, human, subject, cell, tissue, organ, or biological fluid. "Administration" and "treatment" can refer, e.g., to therapeutic, placebo, pharmacokinetic, diagnostic, research, and experimental methods. "Treatment of a cell" encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding composition, or by another cell. "Treatment," as it applies to a human, veterinary, or research subject, refers to therapeutic treatment, prophylactic or preventative measures, to research and diagnostic applications. "Treatment" as it applies to a human, veterinary, or research subject, or cell, tissue, or organ, encompasses contact of an IL-23 agonist or IL-23 antagonist to a human or animal subject, a cell, tissue, physiological compartment, or physiological fluid. "Treatment of a cell" also encompasses situations where the IL-23 agonist or IL-23 antagonist contacts IL-23 receptor (heterodimer of IL-23R and IL-12Rbeta1), e.g., in the fluid phase or colloidal phase, as well as situations where the agonist or antagonist contacts a fluid, e.g., where the fluid is in contact with a cell or receptor, but where it has not been demonstrated that the agonist or antagonist contacts the cell or receptor.

"Binding composition" refers to a molecule, small molecule, macromolecule, antibody, a fragment or analogue thereof, or soluble receptor, capable of binding to a target.

"Binding composition" also may refer to a complex of molecules, e.g., a non-covalent complex, to an ionized molecule, and to a covalently or non-covalently modified molecule, e.g., modified by phosphorylation, acylation, cross-linking, cyclization, or limited cleavage, which is capable of binding to a target. "Binding composition" may also refer to a molecule in combination with a stabilizer, excipient, salt, buffer, solvent, or additive, capable of binding to a target. "Binding" may be defined as an association of the binding composition with a target where the association results in reduction in the normal Brownian motion of the binding composition, in cases where the binding composition can be dissolved or suspended in solution.

"Conservatively modified variants" applies to both amino acid and nucleic acid sequences. With respect to particular nucleic acid sequences, conservatively modified variants refers to those nucleic acids which encode identical or essentially identical amino acid sequences or, where the nucleic acid does not encode an amino acid sequence, to essentially identical nucleic acid sequences. Because of the degeneracy of the genetic code, a large number of functionally identical nucleic acids may encode any given protein. As to amino acid sequences, one of skill will recognize that an individual substitution to a nucleic acid, peptide, polypeptide, or protein sequence which substitutes an amino acid or a small percentage of amino acids in the encoded sequence for a conserved amino acid is a "conservatively modified variant." Conservative substitution tables providing functionally similar amino acids are well known in the art. An example of a conservative substitution is the exchange of an amino acid in one of the following groups for another amino acid of the same group (U.S. Pat. No. 5,767,063 issued to Lee, et al.; Kyte and Doolittle (1982) *J. Mol. Biol.* 157: 105-132):

(1) Hydrophobic: Norleucine, Ile, Val, Leu, Phe, Cys, or Met;
(2) Neutral hydrophilic: Cys, Ser, Thr;
(3) Acidic: Asp, Glu;
(4) Basic: Asn, Gln, His, Lys, Arg;
(5) Residues that influence chain orientation: Gly, Pro;
(6) Aromatic: Trp, Tyr, Phe;
(7) Small amino acids: Gly, Ala, Ser.

"Derived" can be used to describe, e.g., deriving the structure of a peptide, oligopeptide, or polypeptide from a parent peptide, oligopeptide, or polypeptide, such as an antibody. In this context, derived encompasses, e.g., peptide structures where the peptide has the same sequence as a sequence found within the parent, e.g., where the peptide is identical to the parent but with a truncation at the N-terminus, C-terminus, or both N- and C-termini of the parent, or with a truncation and a fusion, or with a fusion only. Derived also encompasses a peptide having the same sequence as found in the parent, but with conservative amino acid changes, or with deletions or insertions, where the deletions or insertions preserve a biological property in the peptide that is inherent in the parent. "Derived" encompasses situations where the peptide or polypeptide is synthesized using the parent as a starting compound, and where the peptide or polypeptide is synthesized de novo, using the structure of the parent as a guide. An example of a "derived" polypeptide is a soluble receptor comprising most or all of the extracellular amino acids of an integral membrane-bound receptor, but not any of the transmembrane segments and not any of the cytosolic segments of the membrane-bound receptor.

"Effective amount" or "therapeutically effective amount" means an amount sufficient to ameliorate a symptom or sign of a disorder or physiological condition or an amount sufficient to permit or facilitate a diagnosis of the disorder or physiological condition. An effective amount for a particular patient or veterinary subject may vary depending on factors such as the condition being treated, the overall health of the patient, the method route and dose of administration and the severity of side affects (see, e.g., U.S. Pat. No. 5,888,530 issued to Netti, et al.). An effective amount can be the maximal dose or dosing protocol that avoids significant side effects or toxic effects. The effect will result in an improvement of a diagnostic measure, parameter, or detectable signal by at least 5%, usually by at least 10%, more usually at least 20%, most usually at least 30%, preferably at least 40%, more preferably at least 50%, most preferably at least 60%, ideally at least 70%, more ideally at least 80%, and most ideally at least 90%, where 100% is defined as the diagnostic parameter shown by a normal subject (see, e.g., Maynard, et al. (1996) *A Handbook of SOPs for Good Clinical Practice*, Interpharm Press, Boca Raton, Fla.; Dent (2001) *Good Laboratory and Good Clinical Practice*, Urch Publ., London, UK).

"Exogenous" refers to substances that are produced outside an organism, cell, or human body, depending on the context. "Endogenous" refers to substances that are produced within a cell, organism, or human body, depending on the context.

"Disorder" refers to a pathological state, or a condition that is correlated with or predisposes to a pathological state. "Infectious disorder" refers, e.g., to a disorder resulting from a microbe, bacterium, parasite, virus, and the like, as well as to an inappropriate, ineffective, or pathological immune response to the disorder. "Oncogenic disorder" encompasses a cancer, transformed cell, tumor, displasia, angiogenesis, metastasis, and the like, as well as to an inappropriate, ineffective, or pathological immune response to the disorder.

"Effective amount" means, e.g., an amount of an IL-23 agonist, IL-23 antagonist, binding compound or binding composition, sufficient to ameliorate a symptom or sign of a disorder, condition, or pathological state. "Effective amount" also relates to an amount of an IL-23 agonist, antagonist, or binding compound or composition, sufficient to allow or facilitate the diagnosis of a symptom or sign of a disorder, condition, or pathological state.

"Inhibitors" and "antagonists" or "activators" and "agonists" refer to inhibitory or activating molecules, respectively, e.g., for the activation of, e.g., a ligand, receptor, cofactor, a gene, cell, tissue, or organ. A modulator of, e.g., a gene, a receptor, a ligand, or a cell, is a molecule that alters an activity of the gene, receptor, ligand, or cell, where activity can be activated, inhibited, or altered in its regulatory properties. The modulator may act alone, or it may use a cofactor, e.g., a protein, metal ion, or small molecule. Inhibitors are compounds that decrease, block, prevent, delay activation, inactivate, desensitize, or down regulate, e.g., a gene, protein, ligand, receptor, or cell. Activators are compounds that increase, activate, facilitate, enhance activation, sensitize, or up regulate, e.g., a gene, protein, ligand, receptor, or cell. An inhibitor may also be defined as a composition that reduces, blocks, or inactivates a constitutive activity. An "agonist" is a compound that interacts with a target to cause or promote an increase in the activation of the target. An "antagonist" is a compound that opposes the actions of an agonist. An antagonist prevents, reduces, inhibits, or neutralizes the activity of an agonist. An antagonist can also prevent, inhibit, or reduce constitutive activity of a target, e.g., a target receptor, even where there is no identified agonist.

To examine the extent of inhibition, for example, samples or assays comprising a given, e.g., protein, gene, cell, or organism, are treated with a potential activator or inhibitor and are compared to control samples without the inhibitor. Control samples, i.e., not treated with antagonist, are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 25%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Endpoints in activation or inhibition can be monitored as follows. Activation, inhibition, and response to treatment, e.g., of a cell, physiological fluid, tissue, organ, and animal or human subject, can be monitored by an endpoint. The endpoint may comprise a predetermined quantity or percentage of, e.g., an indicia of inflammation, oncogenicity, or cell degranulation or secretion, such as the release of a cytokine, toxic oxygen, or a protease. The endpoint may comprise, e.g., a predetermined quantity of ion flux or transport; cell migration; cell adhesion; cell proliferation; potential for metastasis; cell differentiation; and change in phenotype, e.g., change in expression of gene relating to inflammation, apoptosis, transformation, cell cycle, or metastasis (see, e.g., Knight (2000) *Ann. Clin. Lab. Sci.* 30: 145-158; Hood and Cheresh (2002) *Nature Rev. Cancer* 2: 91-100; Timme, et al. (2003) *Curr. Drug Targets* 4: 251-261; Robbins and Itzkowitz (2002) *Med. Clin. North Am.* 86: 1467-1495; Grady and Markowitz (2002) *Annu. Rev. Genomics Hum. Genet.* 3: 101-128; Bauer, et al. (2001) *Glia* 36: 235-243; Stanimirovic and Satoh (2000) *Brain Pathol.* 10: 113-126).

An endpoint of inhibition is generally 75% of the control or less, preferably 50% of the control or less, more preferably 25% of the control or less, and most preferably 10% of the control or less. Generally, an endpoint of activation is at least 150% the control, preferably at least two times the control, more preferably at least four times the control, and most preferably at least 10 times the control.

"Expression" refers to a measure of mRNA or polypeptide encoded by a specific gene. Units of expression may be a measure of, e.g., the number of molecules of mRNA or polypeptide/mg protein, the number of molecules of mRNA or polypeptide/cell, in measurements of expression by cell, tissue, cell extract, or tissue extract. The units of expression may be relative, e.g., a comparison of signal from control and experimental mammals or a comparison of signals with a reagent that is specific for the mRNA or polypeptide versus with a reagent that is non-specific.

"Hybridization" that is specific or selective typically occurs when there is at least about 55% homology over a stretch of at least about 30 nucleotides, preferably at least about 75% over a stretch of about 25 nucleotides, and most preferably at least about 90% over about 20 nucleotides, see, e.g., Kanehisa (1984) *Nucleic Acids Res.* 12: 203-213. Hybridization under stringent conditions, e.g., of a first nucleic acid to a second nucleic acid, are those that: (1) Employ low ionic strength and high temperature for washing, for example, 0.015 M sodium chloride/0.0015 M sodium citrate/0.1% sodium dodecyl sulfate at 50° C.; (2) Employ during hybridization a denaturing agent, such as formamide, for example, 50% (vol/vol) formamide with 0.1% bovine serum albumin/0.1% Ficoll® (Sigma-Aldrich, St. Louis, Mo.)/0.1% polyvinylpyrrolidone/50 mM sodium phosphate buffer at pH 6.5 with 750 mM sodium chloride, 75 mM sodium citrate at 42° C.; (3) Employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 ng/ml), 0.1% SDS, and 10% dextran sulfate at 42° C., with washes at 42° C. in 0.2×SSC and 0.1% SDS; or (4) Employ a buffer of 10% dextran sulfate, 2×SSC (sodium chloride/sodium citrate), and 50% formamide at 55° C., followed by a high-stringency wash consisting of 0.1 X SSC containing EDTA at 55° C. (U.S. Pat. No. 6,387,657 issued to Botstein, et al.).

Stringent conditions for hybridization of nucleic acids are a function of salt, temperature, organic solvents, and chaotropic agents. Stringent temperature conditions will usually include temperatures in excess of about 30° C., more usually in excess of about 37° C., typically in excess of about 45° C., more typically in excess of about 50° C., preferably in excess of about 65° C., and more preferably in excess of about 70° C. Stringent salt conditions will ordinarily be less than about 1 M, more ordinarily less than about 500 mM, usually less than about 400 mM, more usually less than about 300 mM, typically less than about 200 mM, preferably less than about 100 mM, and more preferably less than about 80 mM, even down to less than about 20 mM. However, the combination of parameters is more important than the measure of any single parameter (Wetmur and Davidson (1968) *J. Mol. Biol.* 31: 349-370).

"Immune condition" or "immune disorder" encompasses, e.g., pathological inflammation, an inflammatory disorder, and an autoimmune disorder or disease. "Immune condition" also refers to infections, persistent infections, and proliferative conditions, such as cancer, tumors, and angiogenesis, including infections, tumors, and cancers that resist irradication by the immune system. "Cancerous condition" includes, e.g., cancer, cancer cells, tumors, angiogenesis, and precancerous conditions such as dysplasia.

"Inflammatory disorder" means a disorder or pathological condition where the pathology results, in whole or in part, from, e.g., a change in number, change in rate of migration, or change in activation, of cells of the immune system. Cells of the immune system include, e.g., T cells, B cells, monocytes or macrophages, antigen presenting cells (APCs), dendritic cells, microglia, NK cells, NKT cells, neutrophils, eosinophils, mast cells, or any other cell specifically associated with the immunology, for example, cytokine-producing endothelial or epithelial cells.

"Inflammatory disorder" means a disorder or pathological condition where the pathology results, in whole or in part, from an increase in the number and/or increase in activation of cells of the immune system, e.g., of T cells, B cells, monocytes or macrophages, alveolar macrophages, dendritic cells, NK cells, NKT cells, neutrophils, eosinophils, or mast cells.

"Knockout" (KO) refers to the partial or complete reduction of expression of at least a portion of a polypeptide encoded by a gene, e.g., the p19 subunit of IL-23, where the gene is endogenous to a single cell, selected cells, or all of the cells of a mammal. KO also encompasses embodiments where biological function is reduced, but where expression is not necessarily reduced, e.g., a p19KO polypeptide comprising an expressed p19 polypeptide that contains an inserted inactivating peptide, oligopeptide, or polypeptide. Disruptions in a coding sequence or a regulatory sequence are encompassed by the knockout technique. The cell or mammal may be a "heterozygous knockout", where one allele of the endogenous gene has been disrupted. Alternatively, the cell or mammal may be a "homozygous knockout" where both alleles of the endogenous gene have been disrupted. "Homozygous knockout" is not intended to limit the disruption of both alleles to identical techniques or to identical outcomes at the genome. Included within the scope of this invention is a mammal in which one or both p19 alleles have been knocked out.

"Ligand" refers, e.g., to a small molecule, peptide, polypeptide, and membrane associated or membrane-bound molecule, or complex thereof, that can act as an agonist or antagonist of a receptor. "Ligand" also encompasses an agent that is not an agonist or antagonist, but that can bind to the receptor without significantly influencing its biological properties, e.g., signaling or adhesion. Moreover, "ligand" includes a membrane-bound ligand that has been changed, e.g., by chemical or recombinant methods, to a soluble version of the membrane-bound ligand. By convention, where a ligand is membrane-bound on a first cell, the receptor usually occurs on a second cell. The second cell may have the same or a different identity as the first cell. A ligand or receptor may be entirely intracellular, that is, it may reside in the cytosol, nucleus, or some other intracellular compartment. The ligand or receptor may change its location, e.g., from an intracellular compartment to the outer face of the plasma membrane. The complex of a ligand and receptor is termed a "ligand receptor complex." Where a ligand and receptor are involved in a signaling pathway, the ligand occurs at an upstream position and the receptor occurs at a downstream position of the signaling pathway.

"Memory response" encompasses a method of modulating priming of the immune system. Priming can be accomplished by administering an antigen from a pathogen or cancer cell, while modulation of priming can be accomplished with an agonist of IL-23 or an antagonist of IL-23. Enhancement of priming can be accomplished by administering, e.g., an agonist of IL-23. Increased memory response, i.e., increased priming, encompasses response that are found with or without secondary administration of antigen. Increased memory response, i.e., increased priming, can be measured with or without secondary administration of antigen.

"Sensitivity," e.g., sensitivity of receptor to a ligand, means that binding of a ligand to the receptor results in a detectable change in the receptor, or in events or molecules specifically associated with the receptor, e.g., conformational change, phosphorylation, nature or quantity of proteins associated with the receptor, or change in genetic expression mediated by or associated with the receptor.

"Small molecules" are provided for the treatment of physiology and disorders of tumors and cancers. "Small molecule" is defined as a molecule with a molecular weight that is less than 10 kD, typically less than 2 kD, and preferably less than 1 kD. Small molecules include, but are not limited to, inorganic molecules, organic molecules, organic molecules containing an inorganic component, molecules comprising a radioactive atom, synthetic molecules, peptide mimetics, and antibody mimetics. As a therapeutic, a small molecule may be more permeable to cells, less susceptible to degradation, and less apt to elicit an immune response than large molecules. Small molecules, such as peptide mimetics of antibodies and cytokines, as well as small molecule toxins are described (see, e.g., Casset, et al. (2003) *Biochem. Biophys. Res. Commun.* 307: 198-205; Muyldermans (2001) *J. Biotechnol.* 74: 277-302; Li (2000) *Nat. Biotechnol.* 18: 1251-1256; Apostolopoulos, et al. (2002) *Curr. Med. Chem.* 9: 411-420; Monfardini, et al. (2002) *Curr. Pharm. Des.* 8: 2185-2199; Domingues, et al. (1999) *Nat. Struct. Biol.* 6: 652-656; Sato and Sone (2003) *Biochem. J.* 371: 603-608; U.S. Pat. No. 6,326,482 issued to Stewart, et al).

"Soluble receptor" refers to receptors that are water-soluble and occur, e.g., in extracellular fluids, intracellular fluids, or weakly associated with a membrane. Soluble receptor further refers to receptors that are engineered to be water soluble.

"Specificity of binding," "selectivity of binding," and the like, refer to a binding interaction between a predetermined ligand and a predetermined receptor that enables one to distinguish between the predetermined ligand and other ligands, or between the predetermined receptor and other receptors. "Specifically" or "selectively" binds, when referring to a ligand/receptor, antibody/antigen, or other binding pair, indicates a binding reaction that is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, binds to its antigen with an affinity that is at least two fold greater, preferably at least ten times greater, more preferably at least 20-times greater, and most preferably at least 100-times greater than the affinity to any other antigen. In a preferred embodiment the antibody will have an affinity that is greater than about $10^9$ liters/mol (see, e.g., Munsen, et al. (1980) *Analyt. Biochem.* 107: 220-239).

II. General

The present invention provides methods to modulate immune response to a virus or a viral infection using polypeptides, nucleic acids, variants, muteins, and mimetics of the IL-23 heterodimer, p19 subunit of IL-23, p40 subunit of IL-23 and IL-12, the IL-23 receptor heterodimer, IL-23R subunit, or IL-12Rbeta1 subunit. Also provided are methods for using a hyperkine, i.e., a fusion protein comprising, e.g., the p19 subunit linked to the p40 subunit, as well as nucleic acids encoding the hyperkine (Oppmann, et al. (2000) *Immunity* 13:715-725; Fischer, et al. (1997) *Nature Biotechnol.* 15:142-145; Rakemann, et al. (1999) *J. Biol. Chem.* 274:1257-1266; and Peters, et al. (1998) *J. Immunol.* 161:3575-3581).

Interleukin-23 (IL-23; a.k.a. IL-B30) is a heterodimeric cytokine composed of a novel p19 subunit and the p40 subunit of IL-12 (Oppmann, et al, supra). Like p35, p19 requires co-expression of p40 for biological activity (Wiekowski, et al., (2001) *J. Immunol.* 166:7563-7570). The IL-23 receptor comprises a novel receptor subunit (IL-23R) that binds p19 and IL-12Rbeta1 that binds p40. These two receptor subunits form the functional signaling complex and are expressed on $CD4^+CD45Rb^{lo}$ memory T cells as well as IFNgamma activated bone marrow macrophages (see, e.g., Parham, et al. (2002) *J. Immunol.* 168:5699-5708).

Antibodies can be raised to various cytokine proteins, including individual, polymorphic, allelic, strain, or species variants, and fragments thereof, both in their naturally occurring (full-length) forms or in their recombinant forms. Additionally, antibodies can be raised to receptor proteins in both their native (or active) forms or in their inactive, e.g., denatured, forms. Anti-idiotypic antibodies may also be used.

Administration of an IL-23 agonist, i.e., IL-23 or IL-23 hyperkine, can induce, e.g., proliferation of memory T cells, PHA blasts, CD45RO T cells, CD45RO T cells, or enhance production of interferon-gamma (IFNgamma) by PHA blasts or CD45RO T cells. In contrast to IL-12, IL-23 preferentially stimulates memory as opposed to naïve T cell populations in both human and mouse. IL-23 activates a number of intracellular cell-signaling molecules, e.g., Jak2, Tyk2, Stat1, Stat2, Stat3, and Stat4. IL-12 activates this same group of molecules, but Stat4 response to IL-23 is relatively weak, while Stat4 response to IL-12 is strong (Oppmann, et al., supra; Parham, et al., supra).

IL-12 and IL-23 engage similar signal transduction mechanisms. IL-23 engaging its receptor complex, activates Jak2, Tyk2, and Stat-1, -3, -4, and -5, as does IL-12. However Stat-4 activation is significantly weaker in response to IL-23 than IL-12. Also, in contrast to IL-12, the most prominent Stat induced by IL-23 is Stat-3 (see, e.g., Parham, et al., supra).

Administration of the p19 subunit of IL-23 can result in, e.g., stunted growth, infertility, and death of animals, as well as inflammatory infiltrates, e.g., in the gastrointestinal tract, lungs, skin, and liver, and epithelial cell hyperplasia, microcytic anemia, increased neutrophil count, increased serum TNFalpha; and increased expression of acute phase genes in liver. Enhanced IL-23 expression occured in immortalized not transformed epithelial cell lines (Wiekowski, et al., supra).

Other studies have demonstrated that IL-23 modulates immune response to infection (see, e.g., Pirhonen, et al. (2002) *J. Immunol.* 169: 5673-5678; Broberg, et al. (2002) *J Interferon Cytokine Res.* 22: 641-651; Elkins, et al. (2002) *Infection Immunity* 70: 1936-1948; Cooper, et al. (2002) *J. Immunol.* 168: 1322-1327).

The present invention provides methods to modulate immune response to a virus, including modulating response of $CD4^+$ T cells, CD8' T cells, antigen presenting cells (APCs) such as macrophages and dendritic cells (DCs), B cells, and antibody response. Also provided are methods to modulate response to primary and secondary infections. Both $CD4^+$ T cells and $CD8^+$ T cells have a role in responding to influenza virus infection. $CD4^+$ T cells can respond by lysing infected cells expressing MHC Class II, while $CD8^+$ T cells can respond by lysing infected cells expressing MCH Class I (see, e.g., Epstein, et al. (1998) *J. Immunol.* 160:322-327; Jameson, et al. (1999) *J. Immunol.* 162:7578-7583). In the situation where different viral subtypes invade during primary and secondary infections, immune response can be more dependent on $CD8^+$ T cells (see, e.g., Walzl, et al. (2000) *J. Exp. Med.* 192:1317-1326; Epstein, et al. supra; Murali-Krishna, et al. (1998) *Immunity* 8:177-187).

Moreover, the present invention contemplates methods to protect against pathological immune response to a virus. Pathological conditions that can result with immune response to viral infections include, e.g., eosinophilia of the lung, asthma, and allergies (see, e.g., Walzl, et al. (2000) *J. Exp. Med.* 192: 1317-1326; van Benten, et al. (2001) *Allergy* 56: 949-956; Wohlleben, et al. (2003) *J. Immunol.* 170: 4601-4611).

Furthermore, the present invention contemplates methods to recruit immune cells to the lung, e.g., during infection with a respiratory virus. Note that primary response to respiratory tract viral infections can comprise virus specific $CD8^+$ T cells, and non-specific $CD8^+$ T cells. Although influenza virus often solely infections the lung, immune response includes activation of T cells in non-pulmonary tissues, e.g., the spleen and draining mediastinal lymph nodes (MLNs), and recruitment of these immune cells to the lungs (see, e.g., Topham, et al. (2001) *J. Immunol.* 167: 6983-6990; Roman, et al. (2002) *J. Exp. Med.* 196: 957-968; Doherty, et al. (1997) *Immunol. Rev.* 159: 105-117; Woodland, et al. (2001) *Immunol. Res.* 24: 53-67).

The present invention provides methods of using an IL-23 agonist or antagonist to modulate immune responses that are specific and that are non-specific to viral antigen. Immune reaction to viruses, e.g., influenza virus, includes specific and non-specific responses, as documented by a number of studies of IL-12. IL-12 has been identified as promoting antigen-specific response, e.g., to bacteria and viruses while, consistently, anti-IL-12 antibody has been identified as an inhibitor of antigen-specific response (see, e.g., Cooper, et al. (2002) *J. Immunol.* 168: 1322-1327; Miller, et al. (1995) *J. Immunol.* 155: 4817-4828; Jong, et al. (1997) *J. Immunol.* 159: 786-793; Knutson and Disis (2004) *Clin. Exp. Immunol.* 135: 322-329; Clerici, et al. (1993) *Science* 262: 1721-1724; Lohr, et al. (2002) *Clin. Exp. Immunol.* 130: 107-114; Foss, et al. (2002) *Viral Immunol.* 15: 557-566; Seaman, et al. (2004) *J. Virol.* 78: 206-215; van der Meide, et al. (2002) *Vaccine* 20: 2296-2302).

Inquiries into antigen-specific response to a virus can include measurements of response in terms of, e.g., IFNgamma production as well as of $CD8^+$ T cell proliferation. For example, in the case of lymphocytic choriomeningitis virus, IL-12 supported antigen-specific response manifested by antigen-specific increase in IFNgamma production, though IL-12 was not needed for and did not contribute to antigen-specific $CD8^+$ T cell proliferation (Cousens, et al. (1999) *J. Exp. Med.* 189:1315-1328).

The present invention also contemplates methods to increase B cell response. For example, $CD4^+$ T cells and $CD8^+$ T cells can drive B cell responses to influenza by various mechanisms. Immune responses comprising B cells and antibodies can occur in both primary and secondary viral infections (see, e.g., Sangster, et al. (2003) *J. Exp. Med.* 198: 1011-1021; Graham and Braciale (1997) *J. Exp. Med.* 186: 2063-2068).

The present invention contemplates methods to modulate the response of an antigen presenting cell (APC) to a virus, such as influenza virus. APCs include dendritic cells (DCs), macrophages, and Langerhans cells. The relative importance of DCs versus macrophages can differ in immune responses to primary and secondary infections (see, e.g., Bender, et al. (1995) *J. Exp. Med.* 182: 1663-1671; Crowe, et al. (2003) *J. Exp. Med.* 198: 399-410).

Cytokine response has been documented as part of immune response to influenza. Influenza infection results in production of a number of cytokines, e.g., IL-12, IFNgamma, IL-4, IL-5, IL-1alpha, IL-1beta, IL-6, IL-10, TNF, granulocyte macrophage colony stimulating factor (GM-CSF), and macrophage colony stimulating factor. A number of details on IL-12 are as follows. IL-12, a strong inducer of IFNgamma, induces cytotoxicity of activated CD8+ T cells. IFNgamma induced, e.g., by IL-12, provokes expression of MHC class I antigens by infected target cells, thus enabling CD8+ T cells to recognize the infected cells and kill them. Different antigens may be expressed on different species of MHC. For example, the H-2D$^b$ MHC class I is used to present nucleoprotein and acid polymerase peptides of influenza virus, while the H-2K$^b$ MHC class I is used to present a number of other peptides of influenza virus. Dependence on IL-12 can change during the course of influenza infection. Studies on early and later phases of primary infection revealed that in early primary infection, there is a dependence on IL-12, but later on there is apparently no dependence on IL-12 (see, e.g., Tsurita, et al. (2001) *J. Pharmacol. Exp. Therapeutics* 298: 362-368; Pirhonen, et al. (2002) *J. Immunol.* 169:5673-5678; Monteiro, et al. (1998) *J. Virol.* 72:4825-4831; Julkunen, et al. (2001) *Vaccine* 19:S32-S37; Julkunen, et al. (2001) *Cytokine Growth Factor Revs.* 12:171-180; Mbawuike, et al. (1999) *J. Infect. Dis.* 180:1477-1486; Turner, et al. (2001) *J. Immunol.* 167:2753-2758). Arulandandam, et al. (1999) *J. Infect. Dis.* 180:940-949).

Different viruses can provoke different responses in terms of expression of IL-23. For example, IL-23 plays a part in immune response to ocular herpes simplex virus type-I (HSV-1) and Sendai virus infection, as measured by expression of the p19 subunit (of IL-23) while, in contrast, p19 is not induced in response to influenza A virus (Broberg, et al. (2002) *J. Interferon Cytokine Res.* 22: 641-651; Pirhonen, et al. (2002) *J. Immunol.* 169: 5673-5678).

While IL-12 and IL-23 each have been correlated with immune response to viral infection, therapy with an IL-23 agonist has an advantage over therapy with IL-12, due to lower induction of IFNgamma by IL-23, and lower IFN-gamma-induced toxicity (see, e.g., Lo, et al. (2003) *J. Immunol.* 171:600-607; Leonard, et al. (1997) *Blood* 90:2541-2548; Trinchieri (2003) *Nature Revs. Immunol.* 3:133-146; Cousens, et al. supra; Naylor and Hadden (2003) *Int. Immunopharmacol.* 3:1205-1215; Fernandez, et al. (1999) *J. Immunol.* 162:609-617; Orange, et al. (1995) *J. Exp. Med.* 181:901-914).

In the studies of the present invention, a model for human influenza using influenza virus type A infection in C57BL/6J mice was used for characterizing the antigen-specific CD8+ T cell responses. Primary infections were performed intranasally (i.n.) using the X31 recombinant strain of influenza A virus. For secondary infections mice were primed with an intraperitoneal (i.p.) injection of PR8 strain of influenza A virus and are then re-challenged on day 30 intranasally with the X31 strain. Lungs, spleens and lymph nodes were harvested from the infected mice and analyzed. Whole lung digests were used, rather than bronchoalveolar lavage (BAL), to permit the isolation and detection of all cell types in the lungs of influenza infected mice.

The influence of IL-23 agonists and antagonists on immune response to primary and secondary influenza A infection was studied. Influence of IL-23 agonists and antagonist on memory response was also characterized, where memory response is defined as, e.g., a change in immune response that is provoked by an agonist or antagonist of IL-23 administered during priming. IL-23 agonists took the form of administrations of IL-23 polypeptide. IL-23 antagonists took the form of the p35KO, resulting in a deficiency in IL-12, and the p40KO, resulting in deficiencies in both IL-23 and IL-12. In knockout studies, physiological responses specific for IL-23, rather than to IL-12, can be determined by comparing the physiological responses to the p35KO and p40KO.

Tetramer technology was used to quantitate and phenotype the CD8+ T cells that are specific for the immunodominant influenza virus type A nuclear protein (NP) peptide $NP_{366-374}$. The tetramers complexes are comprised of influenza peptide $NP_{366-374}$-loaded MHC class I (H-2 D$^b$) monomers. Kinetic studies were performed both in primary and secondary influenza virus type A infection.

III. Agonists, Antagonists, and Binding Compositions

The present invention provides methods of using agonists and antagonist of IL-23. An agonist of IL-23 encompasses, e.g., IL-23, an IL-23 variant, mutein, hyperkine, or peptide mimetic thereto, agonistic antibodies to IL-23R, and nucleic acids encoding these agonists. Antagonists of IL-23 include, e.g., antibodies to IL-23, blocking antibodies to IL-23R, a soluble receptor based on the extracellular region of a subunit of the IL-23R, peptide mimetics thereto, and nucleic acids encoding these antagonists.

The present invention provides methods of using agonists and antagonists of p19, the complex of p19 and p40, IL-23R, and the complex of IL-23R and IL-12Rbeta1, including binding compositions that specifically bind to proteins and protein complexes of p19, the complex of p19 and p40, IL-23R, and the complex of IL-23R and IL-12Rbeta1.

An IL-23 hyperkine encompasses, e.g., a fusion protein comprising the polypeptide sequence of p19 and p40, where p1 g and p40 occur in one continous polypeptide chain. The sequences of p19 and p40 may be in either order in the continuous polypeptide chain. The fusion protein may contain a linker sequence, residing in between the sequences of p19 and p40, in one continuous polypeptide chain.

Regions of increased antigenicity can be used for antibody generation. Regions of increased antigenicity of human p19 occur, e.g., at amino acids 16-28; 57-87; 110-114; 136-154; and 182-186 of GenBank AAQ89442 (gi:37183284). Regions of increased antigenicity of human IL-23R occur, e.g., at amino acids 22-33; 57-63; 68-74; 101-112; 117-133; 164-177; 244-264; 294-302; 315-326; 347-354; 444-473; 510-530; and 554-558 of GenBank AAM44229 (gi: 21239252). Analysis was by a Parker plot using Vector NTI® Suite (Informax, Inc, Bethesda, Md.).

Antibodies have been prepared to the subunits of IL-23, IL-12, and to the subunits of the IL-23 and IL-12 receptors. The present invention provides antibodies, and fragments thereof, to p19, p40, p35, IL-23R, IL-12Rbeta1, and IL-12Rbeta2 (see, e.g., Lee, et al. (2004) *J. Exp. Med.* 199: 125-130; Parham, et al. (2002) *J. Immunol.* 168: 5699-5708; Rogge, et al. (1999) *J. Immunol.* 162: 3926-3932; Hoeve, et al. (2003) *Eur. J. Immunol.* 33: 3393-3397; Oppmann, et al. (2000) *Immunity* 13: 715-725; Presky, et al. (1998) *J. Immunol.* 160: 2174-2179). Also contemplated are antibodies that bind to epitopes of both p19 and p40, epitopes of both p35 and p40, epitopes of both IL-23R and IL-12Rbeta1, and epitopes of both IL-12Rbeta1 and IL-12Rbeta2.

Also provided are soluble receptors corresponding to an extracellular domain of IL-23R, IL-12Rbeta1, or IL-12Rbeta2. The present invention also provides an IL-23 antagonist comprising an extracellular region of human IL-23R, for example, amino acids 1-353 of GenBank AAM44229, or a fragment thereof, where the extracellular region or fragment thereof specifically binds to IL-23. Mouse IL-23R is GenBank NP_653131 (gi:21362353) is also available for making a soluble receptor. The sequences of IL-12Rbeta1 and IL-12Rbeta2 are available. Extracellular regions of these receptor subunits comprise amino acids 24-545 of IL-12Rbeta1 (GenBank P42701; GI:1170462) and amino acids 22-624 of IL-12Rbeta2 (GenBank Q99665; GI: 12229836). Soluble receptors based on these extracellular regions are not limited by these exact N-terminal and C-terminal amino acids, but may be longer or shorter, e.g., by one, two, three, or more amino acids, as long as the ligand binding properties are substantially maintained. Fusion proteins based on the soluble receptors are also contemplated, e.g., for facilitating purification or stability.

Monoclonal, polyclonal, and humanized antibodies can be prepared (see, e.g., Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol*. 165: 6205; He, et al. (1998) *J. Immunol*. 160: 1029; Tang, et al. (1999) *J. Biol. Chem*. 274: 27371-27378; Baca, et al. (1997) *J. Biol. Chem*. 272: 10678-10684; Chothia, et al. (1989) *Nature* 342: 877-883; Foote and Winter (1992) *J. Mol. Biol*. 224: 487-499; U.S. Pat. No. 6,329,511 issued to Vasquez, et al.). Muteins and variants of antibodies and soluble receptors are contemplated, e.g., pegylation or mutagenesis to remove or replace deamidating Asn residues.

Purification of antigen is not necessary for the generation of antibodies. Immunization can be performed by DNA vector immunization, see, e.g., Wang, et al. (1997) *Virology* 228: 278-284. Alternatively, animals can be immunized with cells bearing the antigen of interest. Splenocytes can then be isolated from the immunized animals, and the splenocytes can fused with a myeloma cell line to produce a hybridoma (Meyaard, et al. (1997) *Immunity* 7: 283-290; Wright, et al. (2000) *Immunity* 13: 233-242; Preston, et al. (1997) *Eur. J. Immunol*. 27: 1911-1918). Resultant hybridomas can be screened for production of the desired antibody by functional assays or biological assays, that is, assays not dependent on possession of the purified antigen. Immunization with cells may prove superior for antibody generation than immunization with purified antigen (Kaithamana, et al. (1999) *J. Immunol*. 163: 5157-5164).

Antibodies will usually bind with at least a $K_D$ of about $10^{-3}$ M, more usually at least $10^{-6}$ M, typically at least $10^{-7}$ M, more typically at least $10^{-8}$ M, preferably at least about $10^{-9}$ M, and more preferably at least $10^{-10}$ M, and most preferably at least $10^{-11}$ M (see, e.g., Presta, et al. (2001) *Thromb. Haemost*. 85: 379-389; Yang, et al. (2001) *Crit. Rev. Oncol. Hematol*. 38: 17-23; Carnahan, et al. (2003) *Clin. Cancer Res*. (Suppl.) 9: 3982s-3990s).

Soluble receptors comprising the extracellular domains of IL-23R or IL-12Rbeta1 receptor polypeptides are provided. Soluble receptors can be prepared and used according to standard methods (see, e.g., Jones, et al. (2002) *Biochim. Biophys. Acta* 1592: 251-263; Prudhomme, et al. (2001) *Expert Opinion Biol. Ther*. 1: 359-373; Fernandez-Botran (1999) *Crit. Rev. Clin. Lab Sci*. 36: 165-224). Also provided are compositions for siRNA interference (see, e.g., Arenz and Schepers (2003) *Naturwissenschaften* 90: 345-359; Sazani and Kole (2003) *J. Clin. Invest*. 112: 481-486; Pirollo, et al. (2003) *Pharmacol. Therapeutics* 99: 55-77; Wang, et al. (2003) *Antisense Nucl. Acid Drug Devel*. 13: 169-189).

IV. Therapeutic Compositions, Methods

The present invention provides methods for treating or preventing viral infections. These methods can be used in conjunction with a vaccine, e.g., inactivated influenza, live attenuated influenza vaccines, and mucosal vaccines, or a small molecule, e.g., an ion channel blocker, such as amantadine and rimantadine, and a neuramimidase inhibitor, such as zanamivir and oseltamivir. Provided are methods for the treatment and diagnosis of respiratory viruses, including influenza virus, for use in agriculture, as with domestic pigs, livestock, or poultry (see, e.g., van Ginkel, et al. (2000) *Emerging Infectious Diseases* 6: 123-132; Sidwell and Smee (2000) *Antiviral Res*. 48: 1-16; Couch (2000) *New Engl. J. Med*. 343: 1178-1787; Yewdell and Garcia-Sastre (2002) *Curr. Opinion Microbiol*. 5: 414-418; Prober (2002) *Semin. Pediatr. Infect. Dis*. 13: 31-39; Ellis and Zambon (2002) *Rev. Med. Virol*. 12: 375-389; Zambon (2001) *Rev. Med. Virol*. 11: 227-241; Ulmer (2002) *Vaccine* 20 (Suppl. 2):S74-S76; Tollis and Di Trani (2002) *The Veterinary J* 164: 202-215).

To prepare pharmaceutical or sterile compositions including an agonist or antagonist of p 19 or of IL-23, the reagent is mixed with a pharmaceutically acceptable carrier or excipient. Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms. Disperse Systems*, Marcel Dekker, NY; Weiner and Kotkoskie (2000) *Excipient Toxicity and Safety*, Marcel Dekker, Inc., New York, N.Y.).

Selecting an administration regimen for a therapeutic depends on several factors, including the serum or tissue turnover rate of the entity, the level of symptoms, the immunogenicity of the entity, and the accessibility of the target cells in the biological matrix. Preferably, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert, et al. (2003) *New Engl. J. Med*. 348: 601-608; Milgrom, et al. (1999) *New Engl. J. Med*. 341: 1966-1973; Slamon, et al. (2001) *New Engl. J. Med*. 344: 783-792; Beniaminovitz, et al. (2000) *New Engl. J. Med*. 342: 613-619; Ghosh, et al. (2003) *New Engl. J. Med*. 348: 24-32; Lipsky, et al. (2000) *New Engl. J. Med*. 343: 1594-1602).

Antibodies, antibody fragments, and cytokines can be provided by continuous infusion, or by doses at intervals of, e.g., one day, one week, or 1-7 times per week. Doses may be provided intravenously, subcutaneously, topically, orally, nasally, rectally, intramuscular, intracerebrally, or by inhalation. A preferred dose protocol is one involving the maximal dose or dose frequency that avoids significant undesirable side effects. A total weekly dose is generally at least 0.05 μg/kg body weight, more generally at least 0.2 μg/kg, most generally at least 0.5 μg/kg, typically at least 1 μg/kg, more typically at least 10 μg/kg, most typically at least 100 μg/kg, preferably at least 0.2 mg/kg, more preferably at least 1.0 mg/kg, most preferably at least 2.0 mg/kg, optimally at least 10 mg/kg, more optimally at least 25 mg/kg, and most optimally at least 50 mg/kg (see, e.g., Yang, et al. (2003) *New Engl. J. Med*. 349: 427-434; Herold, et al. (2002) *New Engl. J. Med*. 346: 1692-1698; Liu, et al. (1999) *J Neurol. Neurosurg. Psych. 67: 451-456; Portielji, et al. (20003) Cancer Immunol. Immunother. 52: 133-144). The desired dose of a small molecule therapeutic, e.g., a peptide mimetic, natural product, or organic chemical, is about the same as for an antibody or polypeptide, on a moles/kg body weight basis. The desired plasma concentration of a small molecule therapeutic is about the same as for an antibody, on a moles/kg body weight basis.

An effective amount for a particular patient may vary depending on factors such as the condition being treated, the overall health of the patient, the method route and dose of administration and the severity of side affects (see, e.g., Maynard, et al. (1996) *A Handbook of SOPs for Good Clinical Practice*, Interpharm Press, Boca Raton, Fla.; Dent (2001) *Good Laboratory and Good Clinical Practice*, Urch Publ., London, UK).

Typical veterinary, experimental, or research subjects include monkeys, dogs, cats, rats, mice, rabbits, guinea pigs, horses, and humans.

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. Preferably, a biologic that will be used is derived from the same species as the animal targeted for treatment, thereby minimizing a humoral response to the reagent.

Methods for co-administration or treatment with a second therapeutic agent, e.g., a cytokine, steroid, chemotherapeutic agent, antibiotic, or radiation, are well known in the art (see, e.g., Hardman, et al. (eds.) (2001) *Goodman and Gilman's The Pharmacological Basis of Therapeutics*, 10$^{th}$ ed., McGraw-Hill, New York, N.Y.; Poole and Peterson (eds.) (2001) *Pharmacotherapeutics for Advanced Practice:A Practical Approach*, Lippincott, Williams & Wilkins, Phila., PA; Chabner and Longo (eds.) (2001) *Cancer Chemotherapy and Biotherapy*, Lippincott, Williams & Wilkins, Phila., PA). An effective amount of therapeutic will decrease the symptoms typically by at least 10%; usually by at least 20%; preferably at least about 30%; more preferably at least 40%, and most preferably by at least 50%.

The route of administration is by, e.g., topical or cutaneous application, injection or infusion by intravenous, intraperitoneal, intracerebral, intramuscular, intraocular, intraarterial, intracerebrospinal, intralesional, or pulmonary routes, or by sustained release systems or an implant (see, e.g., Sidman et al. (1983) *Biopolymers* 22: 547-556; Langer, et al. (1981) *J. Biomed. Mater. Res.* 15: 167-277; Langer (1982) *Chem. Tech.* 12: 98-105; Epstein, et al. (1985) *Proc. Natl. Acad. Sci. USA* 82: 3688-3692; Hwang, et al. (1980) *Proc. Natl. Acad. Sci. USA* 77: 4030-4034; U.S. Pat. Nos. 6,350,466 and 6,316,024).

V. Kits and Diagnostic Reagents

Diagnostic methods for influenza, based on antibodies, nucleic acid hybridization, and the PCR method, are described. Methods for testing and diagnosis relating to viruses, including respiratory viruses and mucosal viruses such as influenza, include enzyme-based assays, such as influenza virus neuramimidase inhibitors, cell-based assays, e.g., using Madin Darby canine kidney cells, and animal models, e.g., the ferret, mouse, and chicken animal models for influenza infection.

This invention provides polypeptides of IL-23, fragments thereof, nucleic acids of IL-23, and fragments thereof, in a diagnostic kit, e.g., for the diagnosis of viral disorders, including of influenza A, and viral disorders of the respiratory tract and of mucosal tissues. Also provided are binding compositions, including antibodies or antibody fragments, for the detection of IL-23, and metabolites and breakdown products thereof. Typically, the kit will have a compartment containing either a IL-23 polypeptide, or an antigenic fragment thereof, a binding composition thereto, or a nucleic acid, such as a nucleic acid probe, primer, or molecular beacon (see, e.g., Rajendran, et al. (2003) *Nucleic Acids Res.* 31: 5700-5713; Cockerill (2003) *Arch. Pathol. Lab. Med.* 127: 1112-1120; Zammatteo, et al. (2002) *Biotech. Annu. Rev.* 8: 85-101; Klein (2002) *Trends Mol. Med.* 8: 257-260).

A method of diagnosis can comprise contacting a sample from a subject, e.g., a test subject, with a binding composition that specifically binds to a polypeptide or nucleic acid of IL-23 or IL-23 receptor. The method can further comprise contacting a sample from a control subject, normal subject, or normal tissue or fluid from the test subject, with the binding composition. Moreover, the method can additionally comprise comparing the specific binding of the composition to the test subject with the specific binding of the composition to the normal subject, control subject, or normal tissue or fluid from the test subject. Expression or activity of a test sample or test subject can be compared with that from a control sample or control subject. A control sample can comprise, e.g., a sample of non-affected or non-inflamed tissue in a patient suffering from an immune disorder. Expression or activity from a control subject or control sample can be provided as a predetermined value, e.g., acquired from a statistically appropriate group of control subjects.

The kit may comprise, e.g., a reagent and a compartment, a reagent and instructions for use, or a reagent with a compartment and instructions for use. The reagent may comprise an agonist or antagonist of IL-23, or an antigenic fragment thereof, a binding composition, or a nucleic acid in a sense and/or anti-sense orientation. A kit for determining the binding of a test compound, e.g., acquired from a biological sample or from a chemical library, can comprise a control compound, a labeled compound, and a method for separating free labeled compound from bound labeled compound. The control compound can comprise a segment of the polypeptide of p19, p40, IL-23R, IL-12Rbeta1, or a nucleic acid encoding p19, p40, IL-23R, IL-12Rbeta1. The segment can comprise zero, one, two, or more antigenic fragments.

A composition that is "labeled" is detectable, either directly or indirectly, by spectroscopic, photochemical, biochemical, immunochemical, isotopic, or chemical methods. For example, useful labels include $^{32}$P, $^{33}$P, $^{35}$S, $^{14}$C, $^{3}$H, $^{125}$I, stable isotopes, fluorescent dyes, electron-dense reagents, substrates, epitope tags, or enzymes, e.g., as used in enzyme-linked immunoassays, or fluorettes (Rozinov and Nolan (1998) *Chem. Biol.* 5: 713-728).

Diagnostic assays can be used with biological matrices such as live cells, cell extracts, cell lysates, fixed cells, cell cultures, bodily fluids, or forensic samples. Conjugated antibodies useful for diagnostic or kit purposes, include antibodies coupled to dyes, isotopes, enzymes, and metals, see, e.g., Le Doussal, et al. (1991) *New Engl. J. Med.* 146: 169-175; Gibellini, et al. (1998) *J. Immunol.* 160: 3891-3898; Hsing and Bishop (1999) *New Engl. J. Med.* 162: 2804-2811; Everts, et al. (2002) *New Engl. J. Med.* 168: 883-889. Various assay formats exist, such as radioimmunoassays (RIA), ELISA, and lab on a chip (U.S. Pat. Nos. 6,176,962 and 6,517,234).

VI. Uses

The present invention provides methods using agonists and antagonists of IL-23 and IL-23 receptor for the diagnosis, prevention, and treatment of mucosal viruses, respiratory viruses, viruses of the *Orthomyxoviridae* family, influenza virus, measles virus, rhinoviruses, coronaviruses, enteroviruses, adenoviruses, parainfluenza viruses (PIV), respiratory syncytial virus (RSV), and herpes viruses (see, e.g., Mackie (2003) *Paediatr. Respir. Rev.* 4: 84-90; Wilson and von Itzstein (2003) *Curr. Drug Targets* 4: 389-408; Cox, et al. (2004) *Scand. J. Immunol.* 59: 1-15; Wiley, et al. (2001) *J. Immunol.* 167: 3293-3299; Ninomiya, et al. (2002) *Vaccine* 20: 3123-3129; Crowe and Williams (2003) *Paediatric Respiratory Revs.* 4: 112-119; O'Hagan (1998) *J. Pharm. Pharmacol.* 50: 1-10).

Mucosal regions of the body include, e.g., pulmonary, nasal, gastrointestinal, and urogenital mucosa. Viruses resulting in mucosal infections include influenza, herpes, and immunodeficiency viruses. Provided are methods to increase non-antigen specific immunity and antigen-specific immunity to viruses, as well as methods to increase immune response to primary infections, secondary infections, and to increase memory response, to viruses such as influenza virus. Also provided are methods to modulate $CD8^+$ T cell response, including $CD8^+$ T cell mediated cytotoxicity, and $CD8^+$ T cell activation or proliferation, in response to a virus or to a viral antigen.

The broad scope of this invention is best understood with reference to the following examples, which are not intended to limit the inventions to the specific embodiments.

EXAMPLES

I. General Methods

Standard techniques for the characterizing viruses, modification of viruses by genetic engineering, and the treatment and diagnosis of viral infections are available (see, e.g., Mahy and Kango (1996) *Virology Methods Manual*, Academic Press, San Diego, Calif.; Flint, et al. (2003) *Principles of Virology:Molecular Biology, Pathogenesis, and Control of Animal Viruses*, Am. Soc. Microbiol., Wash. D.C.; Fields, et al. (eds.) (2001) *Virology*, Lippincott, Williams, and Wilkins, N.Y., N.Y.; Cann (2001) *Principles of Molecular Virology*, Academic Press, San Diego, Calif.; White and Fenner (1994) *Medical Virology*, $4^{th}$ ed., Academic Press, San Diego, Calif.; Murphy, et al. (1999) *Veterinary Virology*, $3^{rd}$ ed., Academic Press, San Diego, Calif.; Richman, et al. (eds.) (2002) *Clinical Virology*, $2^{nd}$ ed., Am. Soc. Microbiol., Wash. D.C.).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, N.J.; Givan (2001) *Flow Cytometry*, $2^{nd}$ ed.; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (see, e.g., Molecular Probes (2003) *Catalogue*, Molecular Probes, Inc., Eugene, Oreg.; Sigma-Aldrich (2003) *Catalogue*, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.).

Methods for using animal models, e.g., knockout mice, and cell-based assays for the testing, evaluation, and screening of diagnostic, therapeutic, and pharmaceutical agents are available (see, e.g., Car and Eng (2001) *Vet. Pathol.* 38: 20-30; Kenyon, et al. (2003) *Toxicol. Appl. Pharmacol.* 186: 90-100; Deurloo, et al. (2001) *Am. J. Respir. Cell Mol. Biol.* 25: 751-760; Zuberi, et al. (2000) *J. Immunol.* 164: 2667-2673; Temelkovski, et al. (1998) *Thorax* 53: 849-856; Horrocks, et al. (2003) *Curr. Opin. Drug Discov. Devel.* 6: 570-575; Johnston, et al. (2002) *Drug Discov. Today* 7: 353-363).

Standard methods in molecular biology are described (see, e.g., Maniatis, et al. (1982) *Molecular Cloning, A Laboratory Manual*, Cold Spring Harbor Laboratory Press, Cold Spring Harbor, N.Y.; Sambrook and Russell (2001) *Molecular Cloning*, $3^{rd}$ ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York; Ausubel, et al. (2001) *Current Protocols in Molecular Biology*, Vol. 3, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Methods for the production, purification, and fragmentation of polyclonal and monoclonal antibodies are described (Coligan, et al. (2001) *Current Protcols in Immunology*, Vol. 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protcols in Immunology*, Vol. 4, John Wiley, Inc., New York).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne, et al. (2000) *Bioinformatics* 16: 741-742; Menne, et al. (2000) *Bioinformatics Applications Note* 16: 741-742; Wren, et al. (2002) *Comput. Methods Programs Biomed.* 68: 177-181; von Heijne (1983) *Eur. J. Biochem.* 133: 17-21; von Heijne (1986) *Nucleic Acids Res.* 14: 4683-4690).

II. Primary Infection of Wild Type, p35KO Mice and p40KO Mice

Protocols for cytotoxicity assays, intracellular IFNgamma assays, the tetramer method for identifying antigen-specific $CD8^+$ T cells, and for infecting mice are provided (see, e.g., Leander, et al. (2002) *Mechanisms Ageing Devel.* 123: 1167-

1181; Halstead, et al. (2002) *Nature Immunol.* 3: 536-541). CD8+ T cells mediate cell death infected with virus by the perforin/granzyme mechanism or by Fas-mediated cytotoxicity. The $^{51}$Cr-release assay (5 h) is sensitive only to the perforin/granzyme mechanism (Belz, et al. (2000) *J. Virol.* 74: 3486-3493). Studies with infection of mice with influenza virus include use of HKx31 (a.k.a. H3N2), which is a relatively mild strain, and the PR8 strain, which is more virulent (Flynn, et al. (1998) *Immunity* 8: 683-691; Belz, et al. (2000) *J. Virol.* 74: 3486-3493).

Primary infection was induced by administering intranasal X31 recombinant influenza A virus. Infection was induced in wild type mice, p35KO mice (a.k.a. p35$^{-/-}$ mice), which are specifically deficient in IL-12, and p40KO mice (a.k.a. p40$^{-/-}$ mice), which are deficient in both IL-12 and IL-23. Lungs were harvested at t=10 days after inoculation.

The total CD8+ T cells harvested from lungs, during primary infection, increased in the p35KO. No increase occurred in the p40KO mice (Table 1). Although an increase might have been expected in the p40KO mice, because of the lack of IL-12, this rise was prevented by the p40KO, indicating that the additional lack of IL-23 prevented the expected rise in CD8+ T cells. The present invention provides an IL-12 antagonist to stimulate an increase in total CD8+ T cells (Table 1). Also provided is an agonist of IL-23 to stimulate total CD8+ T cells (Table 1).

In addition to modulating the total number of CD8+ T cells, the p35KO and p40KO influenced the percent or proportion of CD8+ T cells that were specific for viral antigen. The proportion or percent of antigen specific CD8+ T cells increased from about 7.0% in the wild type to about 11.5% with the p35KO. The present invention provides an antagonist of IL-12 to stimulate an increase in antigen specific CD8+ T cell response (Table 1).

An increase in antigen specific CD8+ T cell response did not occur in the p40KO, indicating that deficiency in IL-23 prevents increases in antigen specific CD8+ T cells, that is, prevents the same sort of detected increase found with the p35KO (Table 1). Thus, the invention provides an agonist of IL-23 to increase antigen-specific CD8+ T cell response (Table 1).

IFNgamma expression studies provided the following results. The proportion of IFNgamma-producing antigen-specific CD8+ T cells increased from about 9.0% in the wild type, to about 13.0% in the p35KO. Thus, the present invention provides an antagonist of IL-12 to increase the percent of CD8+ T cells that is an antigen-specific CD8+ T cell. This increase did not occur with the p40KO (Table 1). Thus, the present invention provides an agonist of IL-23 to increase IFNgamma-producing antigen-specific CD8+ T cell response (Table 1).

Ex vivo cytotoxicity assays, at effector/target ratios of 50:1, 25:1, 12.5:1, and 6.25:1, all demonstrated lowest cytotoxicity using cells from wild type; intermediate cytotoxicity using cells from the p35KO mice, and greatest cytotoxicity using cells from the p40KO. The results from tests at the 50:1 ratio are shown (Table 1). The present invention provides an antagonist of IL-12, an antagonist of IL-23 to increase antigen-specific cytotoxicity, or the combination of an antagonist to IL-12 and an antagonist to IL-23, to increase antigen-specific CD8+ T cell cytotoxicity (Table 1).

III. Secondary Infection of Wild Type Mice, p35KO Mice, and p40KO Mice

Secondary infection by influenza type A virus was studied in wild type, p35KO mice, and p40KO mice. The protocol for secondary infection involved priming with intraperitoneal PR8 strain of influenza virus at t=day 0, with re-challenge at t=day 30 with intranasal X31 strain of influenza virus. Tissues were harvested at t=day 35, that is, after five days of exposure to the X31 virus (Table 2).

The total number of CD8+ T cells increased in lungs of the p35KO mice, relative to the numbers found in the wild type mice, while this relative increase appeared not to occur in the p40KO mice. Some enrichment in antigen-specific CD8+ T cells was found in the lungs of both the p35KO mice and p40KO mice (Table 2).

TABLE 2

Secondary Infection of Wild Type Mice, p35KO Mice, and p40KO Mice.

| Source of cells | Total CD8+ T cells | % NPP-specific CD8+ T cells | Total NPP-specific CD8+ T cells |
|---|---|---|---|
| Wild type mice | $3.5 \times 10^6$ | 26% | $1.0 \times 10^6$ |
| p35KO mice | $5.0 \times 10^6$ | 32% | $1.65 \times 10^6$ |
| p40KO mice | $3.8 \times 10^6$ | 31% | $1.2 \times 10^6$ |

IV. IL-23 Administration during Primary Infection and Secondary Infection

IL-23 or IL-12 was administered (i.p.) at intervals to mice, as described below. In tests of primary infection, the cytokine was administered starting at the time of intranasal inoculation (Table 3). In tests of secondary infection, the cytokine was administered starting at the time of the re-challenge (Table 4). In tests for memory response, the cytokine was administered starting at the time of the initial priming, but here cytokine was not administered at the time of the re-challenge (Table 5).

Further methodological details were follows. For primary infection, mice were infected intranasally (i.n.) with the X31 strain of influenza A virus and treated with 20 nmole (i.p.) of either IL-23 every other day or with IL-12 every other day.

TABLE 1

Number of CD8+ T cells and proportion of viral-antigen specific CD8+T cells, in cells harvested from lungs in primary infection. IFNgamma production was measured by intracellular staining. Cytotoxicity assays (chromium release) was performed at effector:target ratios of 50:1; 25:1; 12.5:1; and 6.25:1. Table 1 discloses cytotoxicity results at the ratio of 50:1.

| Source of cells | Total CD8+T cells | % NPP-specific CD8+ T cells | Total NPP-specific CD8+ T cells | Total IFNgamma producing CD8+T cells | % NPP$_{366-374}$ specific IFNgamma producing CD8+T cells | Ex vivo cytotoxicity (% Cr release) |
|---|---|---|---|---|---|---|
| wild type | $2.0 \times 10^6$ | 7.0% | $0.15 \times 10^6$ | $0.18 \times 10^6$ | 9.0% | 31% |
| p35KO | $3.6 \times 10^6$ | 11.5% | $0.41 \times 10^6$ | $0.64 \times 10^6$ | 13.0% | 35% |
| p40KO | $1.9 \times 10^6$ | 8.0% | $0.15 \times 10^6$ | $0.22 \times 10^6$ | 9.5% | 39% |

Cytokine treatment was on days 0, 2, 4, 6, and 8. Lungs were harvested on day 10 for use in analysis of immune response, e.g., tests on the quantity and cytotoxicity of CD8+ T cells (Table 3).

For secondary infection, mice were primed (i.p.) with the PR8 strain of influenza A virus (day 0). On day 30 the mice were re-challenged intranasally (i.n.) with the X31 strain of influenza virus and were treated with 20 nmole of either IL-23 (i.p.) or IL-12 (i.p.) every other day. Cytokine treatment was on days 30, 32, and 34. Lungs were harvested was on day 35 for analysis of immune response (Table 4).

For memory response tests, mice were primed with the PR8 strain of influenza virus (i.p.) and treated with 20 nmole of either IL-23 (i.p.) or IL-12 (i.p.) every other day up to day 8. Cytokine treatment was on days 0, 2, 4, 6, and 8. The mice were then re-challenged with the X31 strain of influenza virus (i.n.) on day 30. Lungs were harvested on day 35 for use analysis of immune response (Table 5).

Cytokine administration during primary response to influenza infection provided the following results. In tests of total CD8+ T cell number, the total number of CD8+ T cells was about the same for untreated and for IL-23-treated mice, while the total number of CD8+ T cells was increased in the IL-12-treated mice (Table 3). The proportion of CD8+ T cells that were viral antigen-specific was decreased in the IL-23-treated mice (Table 3). In assays of antigen-specific IFN-gamma producing CD8+ T cells, the results also demonstrated that IL-23 administration decreased the proportion of antigen-specific CD8+ T cells (Table 3). The present invention provides an agonist of IL-23 to decrease the proportion of antigen-specific CD8+ T cells, and an antagonist of IL-23 to increase the proportion of antigen-specific of CD8+ T cells, e.g., during primary infection (Table 3).

Cytotoxicity test results were as follows. In studies of primary infection, administration of IL-23 decreased viral antigen-specific cytotoxicity mediated by CD8+ T cells. The present invention provides an agonist of IL-23 to decrease viral antigen-specific cytotoxicity mediated by CD8+ T cells. Also provided is an antagonist of IL-23 to stimulate or increase viral antigen-specific cytotoxicity mediated by CD8+ T cells (Table 3).

Serum IFNgamma levels were also measured. During the course of primary infection, administration of IL-12, but not of IL-23, increased serum IFNgamma of infected mice, as determined by ELISA assays. At days 1, 3, and 5, after infection, serum IFNgamma in the IL-12-treated mice was about 100, 570, and 130 pg/ml, respectively. Serum IFNgamma levels of non-cytokine treated and IL-23-treated mice were below 50 pg/ml within the time frame studied.

Tests of response to secondary infection also addressed total CD8+ T cells, the proportion of CD8+ T cells that was viral antigen specific, and cytoxicity assays (Table 4). The total number of CD8+ T cells decreased with IL-23 treatment, relative to the number in mice not treated with cytokine, where a greater decrease in total number of CD8+ T cells occurred with IL-12 treatment. The present invention provides a method of using an agonist of IL-23, agonist of IL-12, or agonists of both IL-23 and IL-12, to decrease total number of CD8+ T cells, during secondary infection. Also provided is a method of using an antagonist of IL-23, antagonist of IL-12, or antagonists to both IL-23 and IL-12, to increase the total number of total number of CD8+ T cells, during secondary infection (Table 4).

Administration of IL-23 or IL-12 had little influence on the proportion of total number of CD8+ T cells that was specific for viral antigen, while administration of IL-23 or IL-12 tended to reduce the proportion of CD8+ T cells that were viral antigen-specific IFNgamma producing CD8+ T cells (Table 4).

Cytokine treatment during secondary infection provoked changes in cytotoxicity. Administering IL-23 resulted in a decrease in cytotoxicity, relative to that found with mice not receiving any cytokine, while administering IL-12 resulted in a greater decrease in cytotoxicity (Table 4). The present invention provides methods of administering IL-23 agonist, or IL-23 agonist with IL-12 agonist, to decrease cytotoxicity of antigen-specific CD8+ T cells. Also provided are methods of administering an IL-23 antagonist, or an IL-23 antagonist with an IL-12 antagonist, to increase cytotoxicity of antigen-specific CD8+ T cells.

Serum IFNgamma was about 1000 pg/ml serum, as determined on harvest day of IL-12 treated mice, during secondary infection. Serum IFNgamma was not detected in non-cytokine treated or IL-23-treated mice, during secondary infection.

The memory response study involved treatment with cytokine for several days after initial priming, but with no cytokine treatment at the time of re-challenge (Table 5). IL-23 provoked an increase in total number of CD8+ T cells, where this increase included an increase in the total number of antigen-specific CD8+ T cells, and an increase in the total number of IFNgamma producing antigen-specific CD8+ T cells, while IL-12 treatment provoked an even greater increase in total number of CD8+ T cells. As measured by percent of antigen-specific IFNgamma producing CD8+ T cells, there was a slight increase in this percent with IL-23 treatment, and a greater increase with IL-12 treatment (Table 5).

The present invention contemplates methods to modulate memory response to viral infection, e.g., by administering an agonist or antagonist of IL-23. Provided is a method of using an IL-23 agonist, or the combination of IL-23 agonist and IL-12 agonist, to increase memory response, e.g., as determined by the proportion of antigen specific CD8+ T cells, or the proportion of antigen specific CD8+ T cells that are IFN-gamma positive.

TABLE 3

Primary response with no treatment, IL-23 treatment, or IL-12 treatment. The data reflect measurements of T cells from lungs. IFNgamma determination was with intracellular staining. Cytotoxicity assays (chromium release) was performed at effector:target ratios of 50:1; 25:1; 12.5:1; and 6.25:1. Table 1 depicts cytotoxicity results at the ratio of 50:1.

| Cytokine treatment protocol | Total CD8+ T cells | % NPP-specific CD8+ T cells | Total NPP-specific CD8+ T cells | % NPP$_{366-374}$ specific IFNgamma producing CD8+ T cells. | Total NPP$_{366-374}$ specific IFNgamma producing CD8+ T cells. | Ex vivo cytotoxicity (% Cr release). |
|---|---|---|---|---|---|---|
| No cytokine | $5.0 \times 10^6$ | 13.6% | $0.6 \times 10^6$ | 15.8% | $0.65 \times 10^6$ | 35% |
| IL-23 | $5.5 \times 10^6$ | 8.1% | $0.44 \times 10^6$ | 10.0% | $0.50 \times 10^6$ | 22% |

TABLE 3-continued

Primary response with no treatment, IL-23 treatment, or IL-12 treatment. The data reflect measurements of T cells from lungs. IFNgamma determination was with intracellular staining. Cytotoxicity assays (chromium release) was performed at effector:target ratios of 50:1; 25:1; 12.5:1; and 6.25:1. Table 1 depicts cytotoxicity results at the ratio of 50:1.

| Cytokine treatment protocol | Total CD8$^+$ T cells | % NPP-specific CD8$^+$ T cells | Total NPP-specific CD8$^+$ T cells | % NPP$_{366-374}$ specific IFNgamma producing CD8$^+$ T cells. | Total NPP$_{366-374}$ specific IFNgamma producing CD8$^+$ T cells. | Ex vivo cytotoxicity (% Cr release). |
|---|---|---|---|---|---|---|
| IL-12 | $9.0 \times 10^6$ | 15.2% | $1.3 \times 10^6$ | 17.0% | $1.4 \times 10^6$ | 51% |

TABLE 4

Secondary response (recall response) with no treatment, IL-23 treatment, or IL-12 treatment. The data reflect measurements of T cells from lungs. IFNgamma determination was with intracellular staining. Cytotoxicity assays (chromium release) was performed at effector:target ratios of 50:1; 25:1; 12.5:1; and 6.25:1. Table 1 depicts cytotoxicity results at the ratio of 50:1.

| Cytokine treatment protocol | Total CD8$^+$ T cells | % NPP-specific CD8$^+$ T cells | Total NPP-specific CD8$^+$ T cells | % NPP$_{366-374}$ specific IFNgamma producing CD8$^+$ T cells. | Total NPP$_{366-374}$ specific IFNgamma producing CD8$^+$ T cells. | Ex vivo cytotoxicity (% Cr release). |
|---|---|---|---|---|---|---|
| No cytokine | $10.0 \times 10^6$ | 53% | $5.2 \times 10^6$ | 43% | $3.5 \times 10^6$ | 98% |
| IL-23 | $6.0 \times 10^6$ | 49% | $3.1 \times 10^6$ | 36% | $1.9 \times 10^6$ | 75% |
| IL-12 | $3.0 \times 10^6$ | 50% | $1.6 \times 10^6$ | 34% | $0.86 \times 10^6$ | 60% |

TABLE 5

Memory response with no treatment, IL-23 treatment, or IL-12 treatment. The data reflect measurements of T cells from lungs. IFNgamma determination was with intracellular staining. ND means not determined. Cytotoxicity assays (chromium release) was performed at effector: target ratios of 50:1; 25:1; 12.5:1; and 6.25:1. Table 1 depicts cytotoxicity results at the ratio of 50:1.

| Cytokine treatment protocol | Total CD8$^+$ T cells | % NPP-specific CD8$^+$ T cells | Total NPP-specific CD8$^+$ T cells | % NPP$_{366-374}$ specific IFNgamma producing CD8$^+$ T cells. | Total NPP$_{366-74}$ specific IFNgamma producing CD8$^+$ T cells. | Ex vivo cytotoxicity (% Cr release) |
|---|---|---|---|---|---|---|
| No cytokine | $7.0 \times 10^6$ | 45% | $3.1 \times 10^6$ | 24% | $1.5 \times 10^6$ | ND |
| IL-23 | $12.0 \times 10^6$ | 48% | $5.6 \times 10^6$ | 28% | $2.8 \times 10^6$ | ND |
| IL-12 | $17.0 \times 10^6$ | 53% | $9.3 \times 10^6$ | 38% | $6.2 \times 10^6$ | ND |

All citations herein are incorporated herein by reference to the same extent as if each individual publication, patent application, or patent was specifically and individually indicated to be incorporated by reference including all figures and drawings.

Many modifications and variations of this invention, as will be apparent to one of ordinary skill in the art can be made to adapt to a particular situation, material, composition of matter, process, process step or steps, to preserve the objective, spirit and scope of the invention. All such modifications are intended to be within the scope of the claims appended hereto without departing from the spirit and scope of the invention. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

What is claimed is:

1. A method of modulating CD8$^+$ T cell response to a viral infection comprising administering an effective amount of an antagonist of IL-23, wherein:

i) the antagonist of IL-23 specifically binds to p19 or IL-23R;

ii) the viral infection is caused by:

a) a respiratory virus;

b) a mucosal virus; or c) an influenza virus;

and iii) said modulating CD8$^+$ T cell response comprises increasing the ex vivo cytotoxicity of CD8$^+$ T cells, wherein the antagonist comprises an antibody or a fragment thereof that specifically binds to p19 or IL-23R.

2. The method of claim 1, wherein the antagonist comprises an antibody or a fragment thereof that specifically binds to p19.

3. The method of claim 2, wherein the antibody or a fragment thereof comprises a monoclonal antibody or fragment thereof.

4. The method of claim 1, wherein the viral infection is caused by a mucosal virus.

5. The method of claim 1, wherein the viral infection is caused by:
a) influenza A;
b) influenza B; or
c) influenza C.

6. The method of claim 1, wherein the viral infection comprises:
a) a respiratory syndrome; or
b) pneumonia.

7. The method of claim 1, wherein the antibody or fragment thereof specifically binds to IL-23R.

8. The method of claim 2, wherein the antibody or fragment thereof comprises a humanized antibody or antigen-binding fragment thereof.

9. The method of claim 2, wherein the antibody fragment is an Fab, Fv, or F(ab')2 fragment.

10. The method of claim 7, wherein the antibody or fragment thereof comprises a monoclonal antibody or fragment thereof.

11. The method of claim 7, wherein the antibody or fragment thereof comprises a humanized antibody or antigen-binding fragment thereof.

12. The method of claim 7, wherein the antibody fragment is an Fab, Fv, or F(ab')2 fragment.

13. The method of claim 1, wherein the ex vivo cytotoxicity of $CD8^+$ T cells is measured by chromium release.

* * * * *